(12) United States Patent
Harlan

(10) Patent No.: US 8,758,333 B2
(45) Date of Patent: *Jun. 24, 2014

(54) LASER-ASSISTED GUIDEWIRE HAVING A VARIABLE STIFFNESS SHAFT

(75) Inventor: Kenneth D. Harlan, Peyton, CO (US)

(73) Assignee: The Spectranetics Corporation, Colorado Springs, CO (US)

(*) Notice: Subject to any disclaimer, the term of this patent is extended or adjusted under 35 U.S.C. 154(b) by 1195 days.

This patent is subject to a terminal disclaimer.

(21) Appl. No.: 12/296,270

(22) PCT Filed: Apr. 4, 2007

(86) PCT No.: PCT/US2007/065986
§ 371 (c)(1),
(2), (4) Date: Apr. 7, 2009

(87) PCT Pub. No.: WO2007/115314
PCT Pub. Date: Oct. 11, 2007

(65) Prior Publication Data
US 2009/0221995 A1    Sep. 3, 2009

Related U.S. Application Data

(60) Provisional application No. 60/788,891, filed on Apr. 4, 2006.

(51) Int. Cl.
*A61B 18/18* (2006.01)
(52) U.S. Cl.
USPC .................................. 606/15; 606/7
(58) Field of Classification Search
USPC .............. 600/433, 434, 435, 585, 139–140, 600/121–125; 606/1, 5, 7–19; 604/61, 604/95.01–95.05, 523, 528, 164.01, 164.12, 604/164.13, 166.01, 170.02
See application file for complete search history.

(56) References Cited

U.S. PATENT DOCUMENTS

| | | |
|---|---|---|
| 4,456,017 A | 6/1984 | Miles |
| 4,648,892 A | 3/1987 | Kittrell et al. |
| 4,662,368 A | 5/1987 | Hussein et al. |
| 4,672,961 A | 6/1987 | Davies |
| 4,799,479 A | 1/1989 | Spears |
| 4,819,632 A | 4/1989 | Davies |
| 4,832,024 A | 5/1989 | Boussignac et al. |

(Continued)

FOREIGN PATENT DOCUMENTS

| | | |
|---|---|---|
| EP | 0163502 | 12/1985 |
| EP | 0355996 | 2/1990 |

OTHER PUBLICATIONS

International Search Report for International (PCT) Patent Application No. PCT/US07/65986, mailed Jan. 29, 2008.

(Continued)

*Primary Examiner* — David Eastwood
(74) *Attorney, Agent, or Firm* — Faegre Baker Daniels LLP

(57) ABSTRACT

Embodiments of the present invention comprise a fiber optic guidewire having a hypotube with a plurality of openings that provide variable stiffness and tracking characteristics between at least one proximal segment and one distal segment of the guidewire. In some embodiments, the guidewire further comprises a mandrel disposed within the hypotube, the mandrel cooperating with the optical fibers to permit the distal end of the hypotube to be shaped as desired by a user. Methods of manufacturing and using the guidewire are also disclosed.

22 Claims, 10 Drawing Sheets

(56) References Cited

U.S. PATENT DOCUMENTS

| | | |
|---|---|---|
| 4,834,093 A | 5/1989 | Littleford et al. |
| 4,844,062 A | 7/1989 | Wells |
| 4,846,193 A | 7/1989 | Tremulis et al. |
| 4,848,339 A | 7/1989 | Rink et al. |
| 4,850,351 A | 7/1989 | Herman et al. |
| 4,854,315 A | 8/1989 | Stack et al. |
| 4,911,148 A * | 3/1990 | Sosnowski et al. ........... 600/136 |
| 4,920,967 A | 5/1990 | Cottonaro et al. |
| 4,929,246 A | 5/1990 | Sinofsky |
| 4,932,413 A | 6/1990 | Shockey et al. |
| 4,940,062 A | 7/1990 | Hampton et al. |
| 4,947,864 A | 8/1990 | Shockey et al. |
| 4,958,642 A | 9/1990 | Christian et al. |
| 4,966,596 A | 10/1990 | Kuntz et al. |
| 4,967,745 A | 11/1990 | Hayes et al. |
| 4,988,356 A | 1/1991 | Crittenden et al. |
| 5,009,655 A | 4/1991 | Daignault, Jr. et al. |
| 5,030,217 A | 7/1991 | Harrington |
| 5,035,686 A | 7/1991 | Crittenden et al. |
| 5,045,061 A | 9/1991 | Seifert et al. |
| 5,053,033 A | 10/1991 | Clarke |
| 5,095,911 A | 3/1992 | Pomeranz |
| 5,115,814 A | 5/1992 | Griffith et al. |
| 5,117,839 A | 6/1992 | Dance |
| 5,188,634 A | 2/1993 | Hussein et al. |
| 5,275,151 A | 1/1994 | Shockey et al. |
| 5,437,288 A * | 8/1995 | Schwartz et al. ............ 600/585 |
| 5,451,233 A | 9/1995 | Yock |
| 5,514,128 A | 5/1996 | Hillsman et al. |
| 5,643,251 A | 7/1997 | Hillsman et al. |
| 5,741,429 A | 4/1998 | Donadio, III et al. |
| 6,027,863 A | 2/2000 | Donadio, III |
| 6,352,531 B1 | 3/2002 | O'Connor et al. |
| 6,428,489 B1 | 8/2002 | Jacobsen et al. |
| 6,887,235 B2 | 5/2005 | O'Connor et al. |
| 7,708,704 B2 * | 5/2010 | Mitelberg et al. ............ 600/585 |
| 2008/0015558 A1 | 1/2008 | Harlan |

OTHER PUBLICATIONS

Written Opinion for International (PCT) Patent Application No. PCT/US07/65986, mailed Jan. 29, 2008.

International Preliminary Report on Patentability for International (PCT) Patent Application No. PCT/US07/65986, issued Oct. 8, 2008.

Restriction Requirement for U.S. Appl. No. 11/696,618, mailed Oct. 11, 2011.

Official Action for U.S. Appl. No. 11/696,618, mailed Feb. 16, 2012 8 pages.

Official Action for U.S. Appl. No. 11/696,618, mailed Aug. 30, 2012 5 pages.

Notice of Allowance for U.S. Appl. No. 11/696,618, mailed Dec. 3, 2012 5 pages.

* cited by examiner

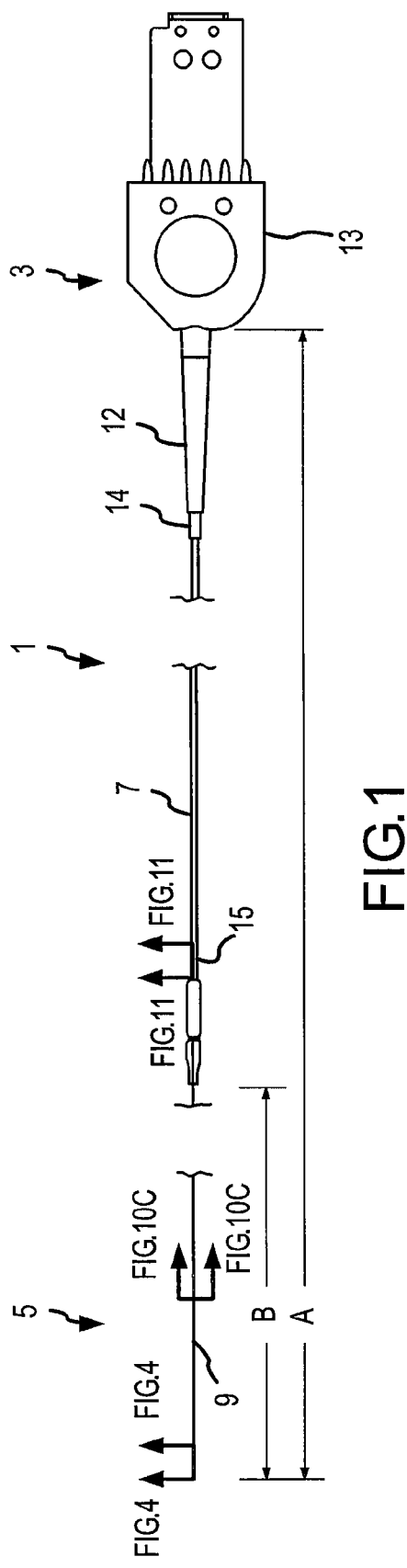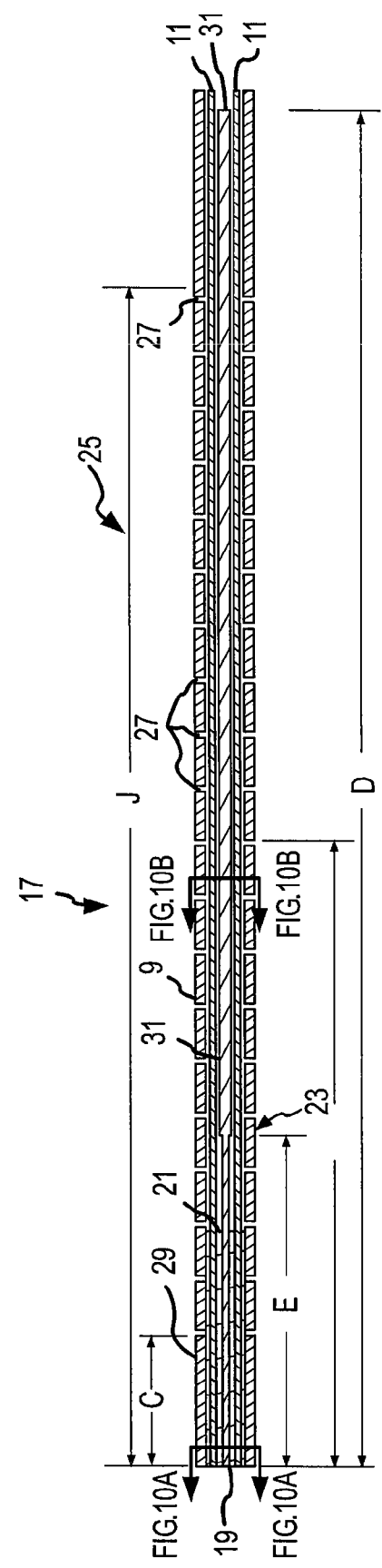
FIG.1
FIG.2

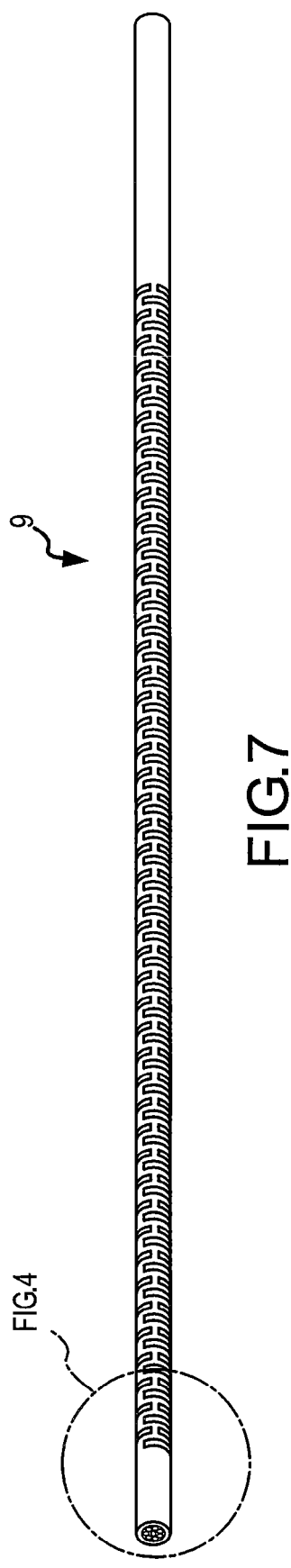
FIG.4
FIG.7
FIG.8

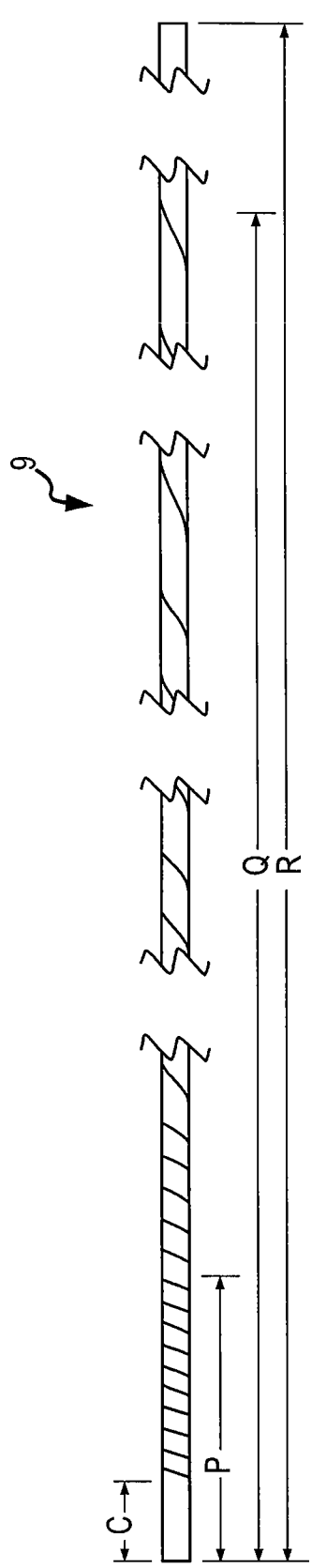
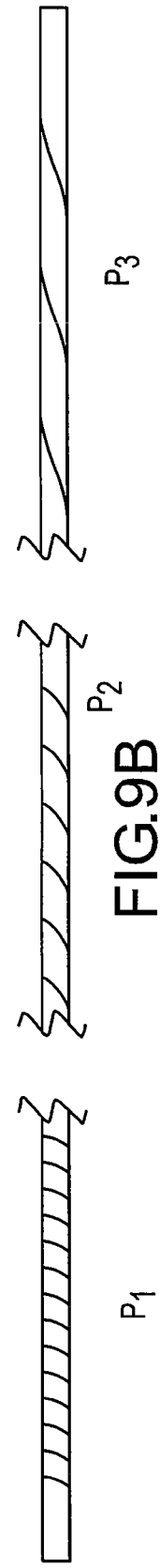
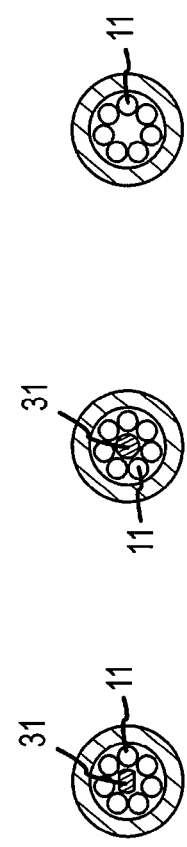
FIG.9A  FIG.9B  FIG.10A  FIG.10B  FIG.10C

LASER-ASSISTED GUIDEWIRE HAVING A VARIABLE STIFFNESS SHAFT

CROSS-REFERENCES TO RELATED APPLICATIONS

This application claims the benefit of U.S. Provisional Patent Application No. 60/788,891 filed Apr. 4, 2006. This application is also related to U.S. Pat. Nos. 5,514,128 and 5,643,251. The entire content of each of these filings is incorporated herein by reference for all purposes.

BACKGROUND OF THE INVENTION

The present invention relates generally to improved devices and methods for the delivery of laser energy within a mammalian subject and, more specifically, to fiber optic guidewires and methods of using same.

Angioplasty and atherectomy are therapeutic medical procedures in which a catheter or the like is inserted into a blood vessel to increase blood flow. In such procedures, a steerable guidewire of relatively small diameter is typically inserted into the patient's blood vessel and moved into proper position past the obstruction. Then a larger treating catheter, as some examples only, a balloon catheter or a laser catheter, is advanced along the guidewire until the catheter is in proper position. The guidewire makes it easier to position the catheter relative to the target site. The catheter is then operated to accomplish its intended purposes. When the catheter and guidewire are withdrawn, the previously obstructed area remains dilated, and blood flow in the target area is increased.

Catheters containing optical fibers transmit energy to irradiate internal parts of the body for diagnostic and therapeutic purposes. There are many medical applications in which it is desirable to deliver energy, such as laser energy, through an optical fiber or similar waveguide device disposed in a body cavity for treatment or diagnosis. These include, among others, the ablation of tissue such as plaque and tumors, the destruction of calculi, and the heating of bleeding vessels for coagulation. The lasers used may produce either pulsed or continuous-wave light of wavelengths ranging from the ultraviolet to the infra-red.

Although a laser catheter can ablate the occlusion, its relatively large diameter sometimes prohibits adequate positioning within the vessel to perform the ablation. Moreover, in some situations, such as with chronic total occlusions, the shape and nature of the vascular occlusion may not permit a guidewire to be positioned so that a laser catheter can be inserted to perform the ablation.

Current mechanical guidewires are limited to mechanical forces transferred to the tip of the device through the shaft in order to create dissections within the vascular occlusions. These mechanical guidewires often cannot cross or penetrate lesions that are often highly calcified in nature, and they do not employ laser energy to facilitate the crossing of vascular lesions. Thus an unmet need remains for a guidewire system that can consistently penetrate and cross chronic total occlusions within the mammalian vasculature with suitable stiffness and torque characteristics.

Embodiments of the present invention provide solutions to at least some of these problems.

BRIEF SUMMARY OF THE INVENTION

The unmet need is met in the present invention by providing a fiber optic guidewire with a hypotube having a proximal end and a distal end, an adhesive plug within the distal end of the hypotube having a distal face substantially flush with the distal end termination of the hypotube, and a plurality of optical fibers disposed within the hypotube, wherein the optical fibers extend through the adhesive plug and have a distal face terminating at the distal face of the adhesive plug. The adhesive plug surrounds the optical fibers and fixes the fibers within the distal end of the hypotube. The hypotube is also comprised of at least one distal segment having an outer surface with a plurality of openings that provides variable stiffness and tracking characteristics between at least one proximal segment and one distal segment of the guidewire. In some embodiments, the guidewire further comprises a mandrel disposed within the hypotube, with a distal end terminating at the distal end of the hypotube, the mandrel cooperating with the optical fibers to permit the distal end of the hypotube to be shaped as desired by a user.

Embodiments of the invention may be maneuvered and positioned in the vasculature like a conventional guidewire using a torque transmitting device. Laser energy from an energy source at the proximal end of the guidewire may be conveyed to the intravascular target area by the optical fibers to ablate an obstruction. Once the guidewire has ablated a passage in the obstruction, its proximal end may be severed distal to the proximal coupler. The tail section and torque device may then be slid off or removed from the severed end, leaving a distal hypotube within the patient. A larger treatment catheter may then be slid over the remaining guidewire to continue the ablation procedure. Additionally, other treatment catheters may be freely loaded on and off the guidewire as needed.

Guidewire systems and method provided herein are well suited for use in treating chronic total occlusions with laser energy. Advantageously, these systems provide handling characteristics of a guidewire and ablation characteristics of a laser delivery device. Embodiments disclosed herein provide efficient and effective solutions for addressing coronary and peripheral chronic total occlusions that may not be crossable or penetrable by standard guidewire modalities. These solutions allow physicians and other system operators to cross vascular lesions in a safe, reliable, and consistent manner.

In one aspect, embodiments of the present invention provide fiber optic guidewire. The guidewire can include, for example, a hypotube having a proximal end and a distal end, an adhesive plug within the distal end of the hypotube and having a distal face substantially flush with the distal end termination of the hypotube, and a plurality of optical fibers disposed within the hypotube. The optical fibers may extend through the adhesive plug and have a distal face terminating substantially at the distal face of the adhesive plug. The adhesive plug can surround the optical fibers and bond the fibers within the distal end of the hypotube. The hypotube can include at least one distal segment having an outer surface with a plurality of openings providing variable stiffness and tracking characteristics between at least one proximal segment and one distal segment of the guidewire. In some cases, the guidewire includes a mandrel disposed within the hypotube. The mandrel can have a distal end that terminates substantially at the distal end of the hypotube. The mandrel can cooperate with the optical fibers to permit the distal end of the hypotube to be shaped as desired by a user. In some cases, the hypotube can include at least one proximal portion having a first stiffness and at least one distal portion having a second stiffness less than the first stiffness. The guidewire may also include a proximal coupler. The hypotube may include stainless steel, Nitinol, or both. In some cases, the guidewire comprises a bending stiffness of about 0.004 grams at or near a location about 1 cm from the distal end of the hypotube corresponding to a deflection distance of about 0.200" in a 1" three point bend stiffness test.

In another aspect, embodiments of the present invention include a fiber optic guidewire. The guidewire can include, for example, a hypotube having a proximal end, a distal end, and a segment or wall having an outer surface with a plurality of openings providing variable stiffness and tracking characteristics to the hypotube. The guidewire may also include two or more optical fibers disposed within the hypotube, and an adhesive plug within the hypotube that surrounds the optical fibers and bonds them to the hypotube. In some cases, the adhesive plug extends radially into at least one of the outer surface openings of the hypotube. The guidewire may also include a mandrel disposed within the hypotube. The hypotube can include at least one proximal portion having a first stiffness and at least one distal portion having a second stiffness less than the first stiffness. In some cases, the hypotube has a flexibility that increases as a linear function of a position along the hypotube extending from a proximal location to a distal location. In some cases, the hypotube has a flexibility that increases as a smooth and continuous function of a position along the hypotube extending from a proximal location to a distal location. The hypotube may include a plurality of hoops such that each hoop is coupled with an adjacent hoop via a brace. In some cases, the length of each hoop is constant. In some cases, the length of each brace is constant. Optionally, the length of each hoop can be smaller than the length of the proximal adjacent hoop. In some cases, the adhesive plug is disposed toward the distal end of the hypotube, and the guidewire further includes a second adhesive plug within the hypotube disposed between the distal and proximal ends of the hypotube. The second adhesive plug can surround the optical fibers and bond them to the hypotube. The guidewire may also include a third adhesive plug within the hypotube disposed toward the proximal end of the hypotube. The third adhesive plug can surround the optical fibers and bond them to the hypotube.

In another aspect, embodiments of the present invention provide a method of manufacturing a guidewire. The method can include, for example, providing a hypotube having a proximal end and a distal end. The hypotube can have a plurality of apertures disposed in a wall of the hypotube between the proximal end and the distal end. The method can also include placing two or more optical fibers at least partially within the hypotube, and introducing an adhesive material into the hypotube. The method may include allowing the material to wick along the optical fibers and into at least one of the plurality of apertures of the wall of the hypotube, such that the adhesive material forms an adhesive plug that fixes the optical fibers relative to the hypotube. In some cases, the method includes inserting a mandrel at least partially within the hypotube. In some cases, the guidewire includes at least one proximal portion having a first stiffness and at least one a distal portion having a second stiffness less than the first stiffness.

For a fuller understanding of the nature and advantages of the present invention, reference should be had to the ensuing detailed description taken in conjunction with the accompanying drawings.

BRIEF DESCRIPTION OF THE DRAWINGS

The present invention will now be described, by way of example, with reference to the accompanying drawings, in which:

FIG. 1 is a side view of one embodiment of the invention.

FIG. 2 is a drawing of cut-away side view of a hypotube of one embodiment of the invention comprising a mandrel.

FIGS. 6A, 6B, and 7 are drawings of one embodiment of a hypotube with segments of similar or differing slot widths.

FIGS. 8, 9A, and 9B are drawings of an embodiments of a hypotube of the invention containing spiraled slots.

FIGS. 10A, 10B, and 10C are a drawings of axial cross-sections of a hypotube of an embodiment of the invention comprising a mandrel, per FIGS. 1 and 2.

Figure 3:
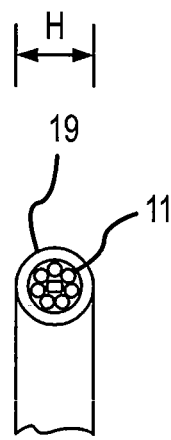
FIG. 3 is a drawing of the distal tip of the guidewire.

It should be noted that the relative sizes and dimensions of elements of the invention are not drawn to scale and may be exaggerated for demonstration purposes.

DETAILED DESCRIPTION OF THE INVENTION

Embodiments of the present invention encompass fiber optic guidewire systems and methods for their use and manufacture. An exemplary fiber optic guidewire includes a hypotube having a proximal end and a distal end, and a plurality of optical fibers disposed within the hypotube. The optical fibers can be anchored or secured to the hypotube with one or more adhesive plugs. The hypotube can include apertures or grooves that provide variable stiffness and tracking characteristics. The fiber optic guidewire may also include a mandrel disposed within the hypotube. Guidewire embodiments disclosed herein can provide steering and torque characteristics that are equivalent to or exceed those observed in other commercially available mechanical guidewires. Moreover, guidewire embodiments disclosed herein provide improved flexibility or stiffness characteristics as compared to other commercially available mechanical guidewires.

Catheter guidewires can include a distal tubular flexible portion. Optical fibers can be disposed within the tubular portion. The guidewire system may include radiopaque markers near or toward the distal end, or at any desired location on the system. The tubular portion or hypotube may include openings such as slots, slits, spiral cuts, and the like, so as to provide desired force transmission, torsional control, and tip shaping capabilities, as well as variable stiffness and tracking characteristics, to the guidewire system. In use, the guidewire can be maneuvered into a vascular area and laser energy can be transmitted through optical fibers disposed within the hypotube, toward a vascular obstruction.

Turning now to the drawings, in some embodiments, without limitation, the invention comprises a fiber optic guidewire 1 with a proximal end 3 and a distal end 5. The guidewire 1 includes a tail tube 7 and a hypotube 9, with a plurality of optical fibers 11 disposed longitudinally therein as shown, for example, in FIGS. 1 and 2. The device comprising the invention may be of any suitable length A, with a length A between about 350 cm and about 390 cm preferred in some embodiments. The tail tube 7 can include plastic tubing that connects at its proximal end to a proximal coupler 13 with heat shrink 14 and strain relief 12. The tail tube 7 can be configured to interface with the hypotube 9 over an exchange lead 15, as further illustrated in FIG. 11. The hypotube segment 9 of the guidewire 1 can be a tubular element having a plurality of optical fibers 11 disposed therein from its proximal end to its distal end. The hypotube segment 9 may be of any suitable length B, with a preferred length of between 160 and 180 cm in some embodiments. The hypotube 9 typically has at least one flexible distal segment 17.

In some embodiments, the plurality of optical fibers 11 disposed within the guidewire extend from or between its proximal end to its distal end. The optical fibers 11 can be polyimide-buffered optical fibers each having a diameter of about 25 to about 75 microns, with fibers of about 50 microns preferred in some embodiments. In some preferred embodiments, the invention is comprised of seven fibers 11 disposed within at least part of the longitudinal length of the guidewire. The number of individual fibers, their corresponding diameter, and their type, can be selected according to desired flexibility characteristics of the hypotube or guidewire. Fiber flexibility can be defined as the force that is needed to deflect a fiber through a given distance. In many cases, this amount of force is observed to increase with the fourth power of the fiber diameter. The flexibility of a bundle of fibers can be increased by reducing the diameter of the fibers in the bundle, because the fiber area increases with the square of the diameter. For example, a bundle of four fibers, each having a diameter of 100 microns, provides a fiber area equivalent to a single fiber having a diameter of 200 microns. The bundle and the single fiber can deliver the same amount of light energy (due to equivalent total cross sectional areas), yet the bundle is four times as flexible as the single fiber.

In manufacturing the guidewire 1, optical fibers of the selected size(s) and number are typically unspooled and stranded together in the desired lengths. The bundled optical fibers 11 are disposed within the tail tube 7, exchange lead 15, and hypotube 9. In some embodiments, at the proximal end 3 of the guidewire, the proximal ends of the optical fibers 11 are connected into a proximal coupler 13. The proximal coupler 13 may then be inserted into an energy source (not shown).

Figure 4:
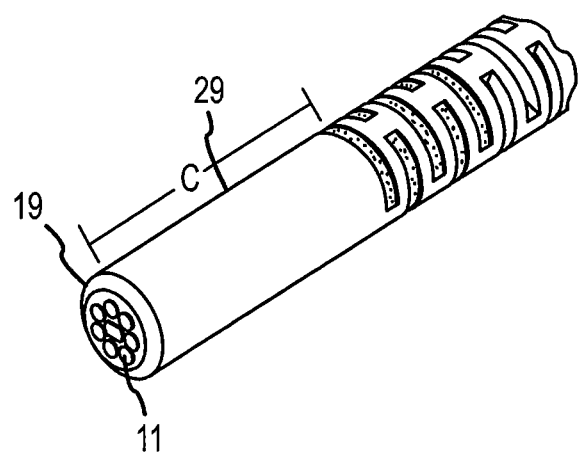
FIG. 4 is a drawing of the distal tip of one embodiment of the guidewire.

In some embodiments, at their distal ends the optical fibers 11 terminate at a tip 19 at the most distal end of the guidewire. The optical fibers 11 can be potted in an adhesive plug 21 extending proximally from the distal end of the hypotube for up to about 1 cm, with about 0.2 cm in some preferred embodiments. In some embodiments, optical fibers 11 can be potted at one or more locations along the length of hypotube 9. For example, optical fibers 11 can be potted in adhesive or otherwise fixed to hypotube 9 at a distal location along the hypotube 9, at a proximal location along hypotube 9, at an intermediate location along hypotube 9 between the distal and proximal locations, or any desired combination thereof. Suitable potting adhesives are known to those of ordinary skill in the art. In some cases, a potting adhesive includes an epoxy material. Often, an adhesive material is selected to provide at least a certain minimum hardness characteristic, or relatedly to provide sufficient durability so as to withstand any degradative effect produced by the ablative energy that travels through the fiber optic bundle. Typically, an adhesive that has a higher hardness value will impart a greater degree of stiffness to the guidewire, as compared to an adhesive with a lower hardness. Guidewire sections that contain adhesive are usually less flexible than guidewire sections having no adhesive, as an adhesive plug can provide a non-deflecting or a minimally deflecting characteristic to the guidewire. In some embodiments, the distal faces of the adhesive plug 21 and the optical fibers 11 terminate substantially co-extensively with the distal face of the hypotube 9, for example as shown in FIGS. 2, 3, and 4. After potting, the distal end of the tip 19 may be ground and polished according to methods known to those of ordinary skill in the art. The distal tip may be beveled to provide a less traumatic profile in some embodiments. As shown in FIG. 3, the outer diameter H of the distal tip of the hypotube can be within a range of about 0.0125" to about 0.0145". In some cases, outer diameter H is about 0.0135" or about 0.014". The outer diameter can be inclusive of any radiopaque coatings and hydrophilic coatings disposed on the hypotube. The individual diameter of each fiber can be about 50 microns.

Optionally, the outer diameter of the distal tip can be between about 0.005 and about 0.018 inches, with an outer diameter of about 0.014 inches in some preferred embodiments. A distal segment 23 of the guidewire comprising the tip may be coated with or otherwise incorporate a radiopaque material, as one example only, with gold plating for a desired length F. In some cases, length F is about 3 cm. The radiopaque material can be incorporated into the hypotube, an adhesive plug, a mandrel, or any other component of the fiber optic guidewire, at any location on the component. In some cases, the radiopaque material is gold, platinum, or some other fluoroscopically detectable substance. In some embodiments, a hypotube is coated or plated with a layer of gold of about 1 to about 2 microns in thickness. In some embodiments, a hypotube is coated with a layer of gold of about 3 to about 4 microns in thickness. In some embodiments, a hypotube is coated with a layer of gold of about 5 to about 6 microns in thickness. In some embodiments, a hypotube is covered with a slippery, smooth, or lubricious material. Exemplary hydrophilic polymer coatings or materials that may be used for a hypotube covering are produced by Surmodics, Inc. of Eden Prairie, Minn.

Figure 5:
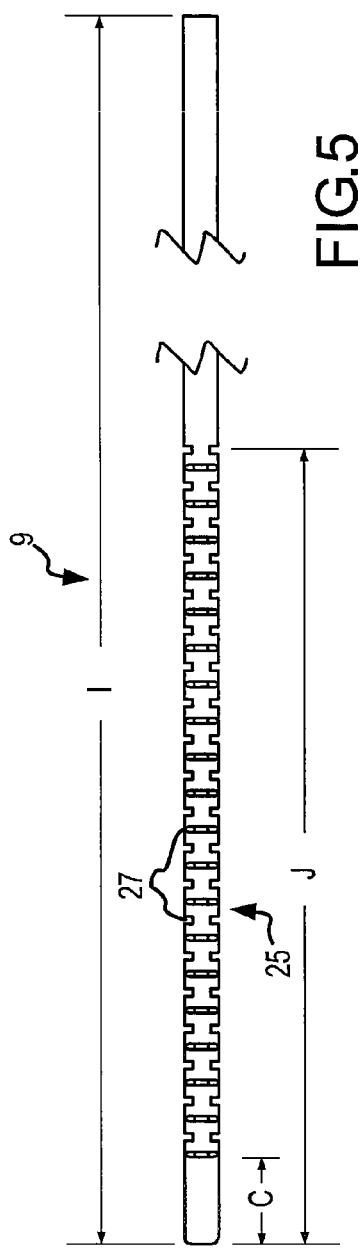
FIG. 5 is a side view of a hypotube.

In preferred embodiments, without limitation, at least some portion 25 of the outer surface of the hypotube 9 comprises a plurality of openings 27 for providing desired variations in stiffness along at least some length of the hypotube, for example as shown in FIGS. 2 and 5. For example, a slotted section 25 of the hypotube 9 can extend proximally from the distal end of the catheter for a distance J, which can be about 30 cm. The openings may comprise slots, slits, spirals, apertures, or other configurations suitable for these purposes. In some embodiments, the hypotube includes a material or structure in place at least some of the openings, whereby the material or structure is compressible and confers flexibility to the hypotube when the guidewire is bent, deflected, or otherwise guided through the vasculature of a patient. In some embodiments, a hypotube may include a compressible elastomer, a flexible adhesive, or a deformable plastic or other material where the aperture or opening would otherwise be located. In some cases, a hypotube may include such elements or a thin wall between hoops and braces of the hypotube so as to impart desired flexibility characteristics to the guidewire. Accordingly, the hypotube may be devoid of openings or apertures.

The hypotube 9 may be made of metal, plastic, polymers, or any combination thereof. In some preferred embodiments, the hypotube 9 is constructed of stainless steel or nickel-titanium alloy, such as Nitinol. The openings 27 may be formed by grinding, cutting, molding, etching, laser cutting, or other methods known to those of ordinary skill in the art. Optionally a low-friction substance, such as PTFE or a similar lubricant, may be applied to the exterior surface of the hypotube, along length B as shown in FIG. 1. The low friction substance can be applied to the entire length of the hypotube, or to one or more discrete sections of the hypotube. As shown in FIG. 5, hypotube 9 has a length I which can be within a range from about 74.58 cm to about 75.18 cm. For example, length I can be about 74.88 cm.

In some embodiments, measuring longitudinally from the distal end of the guidewire, the hypotube may include a solid, unslotted surface 29 having a length C up to about 0.3 cm. In some cases, length C can be up to about 0.085 cm. See, for example, FIGS. 2, 4, 5 and 6A. Thereafter, continuing proximally along the guidewire 1, the hypotube 9 may comprises slots or other suitable openings 27 or compressible elements at predetermined intervals. The adhesive plug 21 at the distal end of the hypotube 9 can be formed in the unslotted portion and may be wicked down selectively into the first few openings 27 of the hypotube 9. The guidewire can also include a mandrel 31, as shown in FIG. 2. Mandrel 31 can extend proximally from the distal end of the catheter for a distance D. In some preferred embodiments, without limitation, distance D can be between about 34.92 cm and about 36.20 cm. For example, distance D can be about 35.56 cm. The outer surface of the hypotube may be of uniform outer diameter or optionally may be tapered along its length. For example, a more proximal section of the hypotube may have a larger diameter, whereas a more distal section of the hypotube may have a relatively smaller diameter. In some embodiments, a more proximal section of the hypotube may have a larger outer diameter, whereas a more distal section of the hypotube may have a relatively smaller outer diameter. Similarly, in some embodiments, a more proximal section of the hypotube may have a smaller inner diameter, whereas a more distal section of the hypotube may have a relatively larger inner diameter.

Figure 6A:
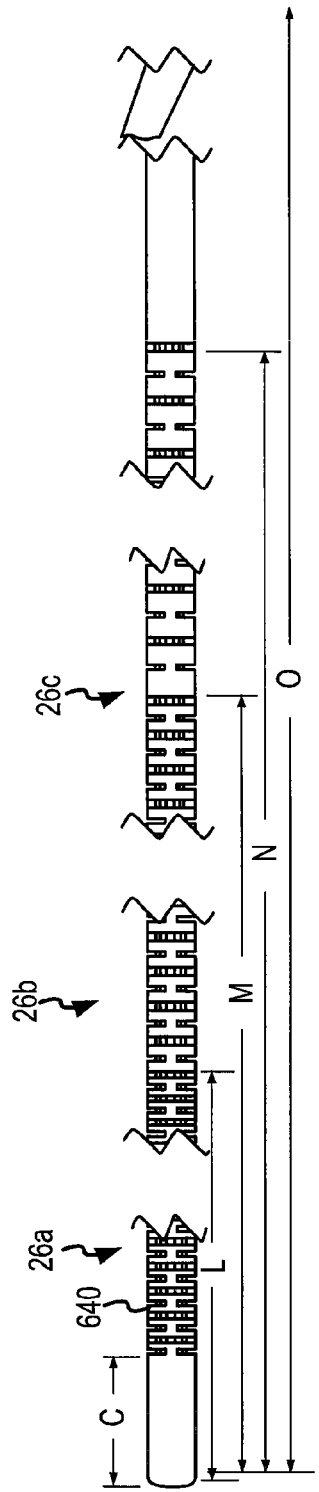

As illustrated in FIG. 6A, in some embodiments a hypotube can have a length O of about 190 cm. The hypotube includes a proximal portion, having a length C, that has no openings. Length C can be about 0.0400". The hypotube also includes a first slotted hypotube section 26a, a second slotted hypotube section 26b, and a third slotted hypotube section 26c. The first slotted hypotube section 26a can have a distal end which is disposed at a length C from the distal tip of the hypotube, and a proximal end which is disposed at a distance L from the distal tip of the hypotube. Distance L can have a length of about 1 cm. In the first slotted hypotube section 26a, each of the hoops 640 of the hypotube have a first hoop length $HL_1$. The second slotted hypotube section 26b can have a distal end which is disposed at a length L from the distal tip of the hypotube, and a proximal end which is disposed at a distance M from the distal tip of the hypotube. Distance M can have a length of about 15 cm. In the second slotted hypotube section 26b, each of the hoops 640 of the hypotube have a second hoop length $HL_2$. The third slotted hypotube section 26c can have a distal end which is disposed at a length M from the distal tip of the hypotube, and a proximal end which is disposed at a distance N from the distal tip of the hypotube. Distance N can have a length of about 30 cm. In the third slotted hypotube section 26c, each of the hoops 640 of the hypotube have a third hoop length $HL_3$. As shown in FIG. 6A, HL1 is smaller than HL2, and HL2 is smaller than HL3. A hypotube having such a configuration can provide a flexibility profile similar to the one shown in FIG. 16, where the flexibility of the hypotube changes as a discontinuous stepwise function at locations along the length of the hypotube.

Figure 6B:
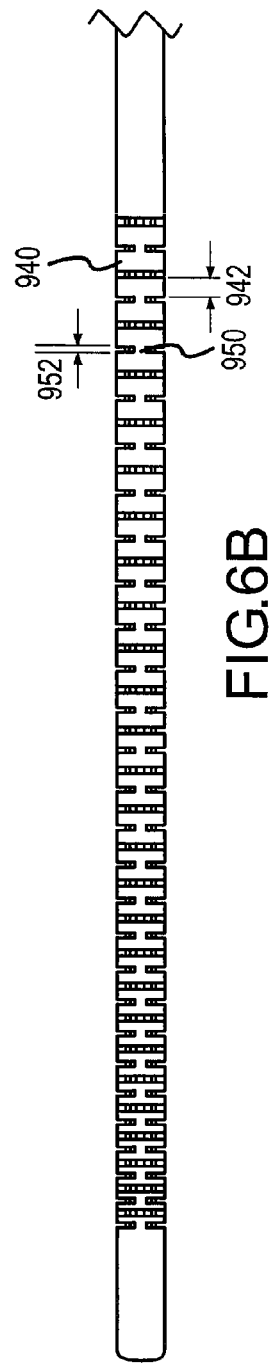

FIG. 6B shows a hypotube configuration where the hoop length 942 of each successive hoop 940 is shorter than the hoop length of the neighboring proximal hoop, and each brace 950 has the same brace length 952. A hypotube having such a configuration can provide a flexibility profile similar to the one shown in FIG. 17, where the flexibility of the hypotube changes as a linear function at locations along the length of the hypotube. Optionally, a hypotube can have a configuration where the hoop length 942 of each successive hoop is constant, and the brace length 952 of each successive brace 950 is longer that the brace length of the neighboring proximal brace. Such a configuration can also provide a flexibility profile similar to the one shown in FIG. 17. FIG. 7 shows an exemplary hypotube configuration according to embodiments of the present invention.

In some embodiments, without limitation, a slotted segment of hypotube may extend proximally from the distal end of the guidewire for a distance up to about 60 cm. In some embodiments, the slotted segment of the hypotube comprises at least 2 slotted segments of differing spatial separation of slots, as shown in FIGS. 8, 9A, and 9B. For example, the pitch or spacing between apertures or grooves in the hypotube can be smaller at the distal section and larger at the proximal section. In some embodiments, the pitch at a more distal section of the hypotube is about 0.012" and the pitch at a more proximal section of the hypotube is about 0.072". The spacing of the pitch may change in a linear pattern in relationship to the length of the hypotube, so that the pitch gradually becomes larger toward the proximal end. In some cases, the spacing of the pitch may change in a non-linear but otherwise smooth and continuous relationship to the length of the hypotube, again so that the pitch gradually becomes larger toward the proximal end. In some cases, discrete sections of the hypotube provide apertures or grooves at a constant pitch, and the hypotube includes one or more sections of varying pitch. The hypotube may also comprise a spiral of uniform or non-uniform pitch, for example as shown in FIGS. 8, 9A, and 9B. A hypotube having a spiral pitch configuration as shown in FIG. 9B, for example, by be constructed by cutting a spiral groove in a tubular member. The width of the spiral groove may vary along the length of the tube. For example, the width of the groove may be greater at the distal end of the tube, and narrower at the proximal end of the tube. Optionally, the spiral cut can be made in the hypotube so as to provide a constant pitch or a variable pitch along the length of the hypotube. In some embodiments, a hypotube comprises a ribbon of material having a constant width. In some embodiments, a hypotube comprises a ribbon of material having a width that continuously and smoothly increases toward the proximal end of the hypotube. Similarly, in some embodiments a hypotube comprises a ribbon of material having discrete sections where the width of each successive section is larger than the width of the adjacent distal section. In some embodiments such a hypotube can have an outer diameter of about 0.014" and an inner diameter of about 0.0085". As shown in FIG. 9A, a distal portion of the hypotube can have a section where the groove or aperture pitch is constant, the section having a proximal end that is disposed at a distance P from the distal end of the hypotube. Here, the pitch is about 0.012". Distance P can have a length within a range from about 1.10" to 1.26". For example, distance P can be about 1.18". The hypotube can also have another section where the pitch varies at distances along the length of the hypotube. For example, a distal end of a variable pitch section can be at a distance P from the distal end of the hypotube, and extend to a distance Q from the distal end of the hypotube. Distance Q can have a length within a range from about 11.4" to about 12.2". For example, distance Q can be about 11.8". The hypotube can have a length R within a range from about 58.5 to about 59.5. For example, length R can be about 59". The slot width, or span of the aperture, can be within a range from about 0.001 inch to about 0.002 inch. In some embodiments, a hypotube having a spiral cut, groove, or aperture can also have one or more struts or braces spanning the cut or aperture (similar to the braces shown in FIG. 12) so as to provide a longitudinal connection between neighboring loops or hoops of the spiral hypotube. A strut can have a width of, for example, 0.011". Struts can be disposed along a spiral hypotube at every 450 degrees. The hypotube may include other strut width and spacing configurations so as to provide a desired flexibility profile. In general, a spiral hypotube having struts placed at every 50 degrees is less flexible than a spiral hypotube having struts placed at every 450 degrees. Similarly, a strut having a width of 0.009" will impart more flexibility than a strut having a width of 0.011". As shown in FIG. 9B, a hypotube can have a first section $P_1$ with a first spiral pitch, a second section $P_2$ with a second spiral pitch, and a third section $P_3$ with a third spiral pitch.

In some embodiments, without limitation, the optical fibers are disposed within at least a portion of the hypotube 9 around a core mandrel 31, for example as shown in FIG. 2. The mandrel 31 may extend within the hypotube 9 proximally from the distal end for a length D. In some embodiments, length D can be between about 30 cm and about 40 cm. For example, length D can be about 35.5 cm. The mandrel 31 may be tapered, with its most distal end or portion flattened and rectangular in cross-section for a distance E. In some embodiments, distance E is between 0.1 and 2 cm. For example, distance E can be about 1.5. FIG. 10A shows a cross section along the hypotube at the location indicated in FIG. 2, where the optical fibers 11 are shown in a circumferential arrangement around mandrel 31. The cross-section of mandrel 31 is shown as having two opposing flattened sides and two opposing circular or arcuate sides. FIG. 10B shows a cross section along the hypotube at the location indicated in FIG. 2, where the optical fibers 11 are shown in a circumferential arrangement around mandrel 31. The cross-section of mandrel 31 is shown as a circle. FIG. 10C shows a cross section along the hypotube at the location indicated in FIG. 1, where the optical fibers 11 are shown in a circumferential arrangement within the hypotube, without an inner mandrel. In some embodiments, the distal end of the flattened portion of the mandrel is substantially central to and coterminal with the terminal face of the hypotube. The distal end of the mandrel can be mounted in the adhesive plug 21 and provide shapeability and durability to the guidewire. The adhesive plug can fix the distal ends of optical fiber bundle and the mandrel in place within the hypotube.

The mandrel may have an intermediate portion which tapers to the flattened distal portion. The proximal end of the mandrel, along with the optical fibers, can be potted in another adhesive plug formed by inserting adhesive into, for example, the most proximal opening 27 in the hypotube. In some embodiments, without limitation, the mandrel is fabricated from stainless steel or tungsten and can be either a tapered or nontapered mandrel. Its outer diameter may range from about 0.002 in. to about 0.005 in., with a length of about 1.5 cm to about 190 cm. The flattened portion can have a rectangular cross-section and can cooperate with the optical fibers to allow the guidewire to be shaped and reshaped to bend at a desired angle, for example as shown in FIGS. 2 and 10A.

Figure 11:
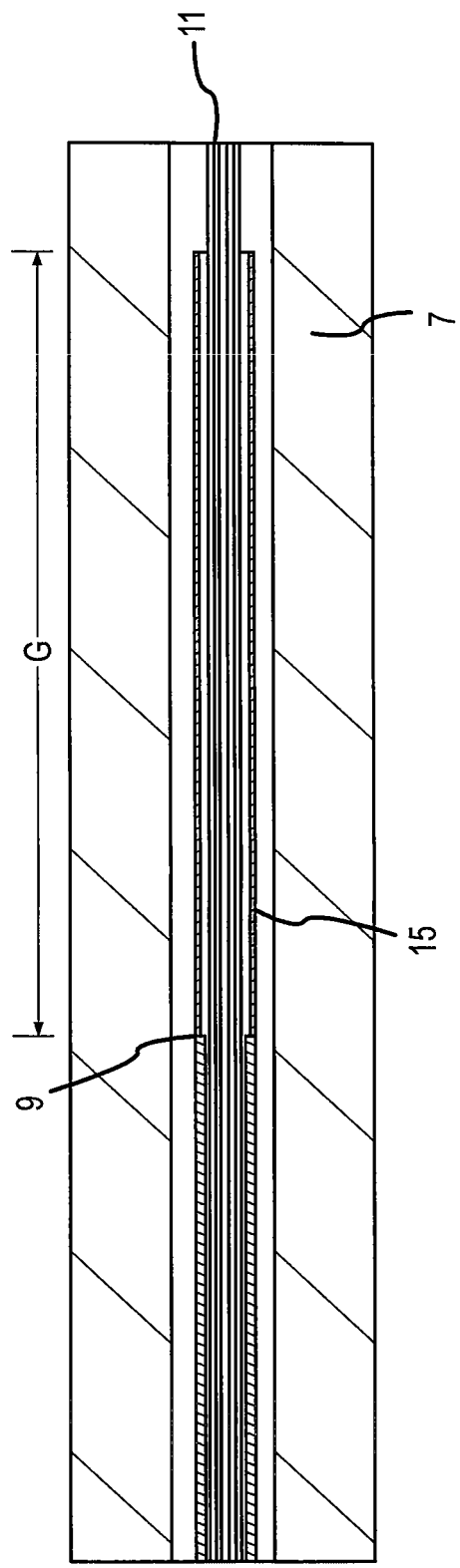
FIG. 11 is a drawing of a side cross-sectional view of an exchange lead segment of the invention.

As shown in FIG. 11, which corresponds to the location indicated in FIG. 1, the proximal end of the hypotube 9 can be configured to interface with the tail tube 7. In some embodiments, a tubular clear exchange lead 15 is disposed over the optical fibers 11 at the proximal end of the hypotube 9. The exchange lead 15 can have a length G, where length G is within a range from about 5 cm to about 9 cm. For example, length G can be about 7 cm. A suitable adhesive, which will be known to those of ordinary skill in the art, can be applied to the proximal end of the hypotube 9 to pot the optical fibers 11 in place. Similarly, a suitable adhesive can be applied to the adjacent distal end of the exchange lead 15, thereby joining it with the hypotube 9.

As shown in FIG. 1, some embodiments of the present invention further comprise a torque knob 37 disposed on the guidewire. The torque knob may be of any suitable configuration known to those of ordinary skill in the art. The torque knob may be positioned at almost any location along the shaft of the hypotube for ease of handling, torquing, and steering during a procedure. When the torque knob is tightened onto the hypotube, the torque knob may be rotated to apply torque to the guidewire. The distal end of the tail tube can interface insertably with an interior segment of the torque knob.

The guidewire may be advantageously used to ablate an intravascular occlusion and/or to position a catheter. As one example only, the guidewire is connected to a source of laser energy by way of proximal coupler. The hypotube segment of the guidewire is maneuvered into the vasculature like a conventional guidewire and positioned so that the distal tip is proximate to the target site. Energy from the laser source is transmitted through the optical fiber bundle to the tip, thereby ablating a channel through the occlusion. Optionally, once a channel has been ablated, the guidewire may be cut at or near the exchange lead, the proximal end of the guidewire and torque knob removed, and the guidewire segment remaining in the patient may be used as a mechanical guidewire to guide a larger catheter or other device for further treatment. The proximal end of the newly-severed optical fibers is pulled away from exchange lead and then detached so that the fibers retract inside the hypotube. A catheter may then be placed on the proximal end of the hypotube and slid down to the point of entry over the hypotube into the patient's body. The catheter is then introduced into the patient's body and slid along the hypotube until it reaches the desired target near the partially-ablated occlusion. With this procedure, a laser catheter may be used to ablate a larger area of the occlusion. Numerous variations of and substitutions for the above-described method will be readily apparent to one of ordinary skill in the art.

Figure 12:
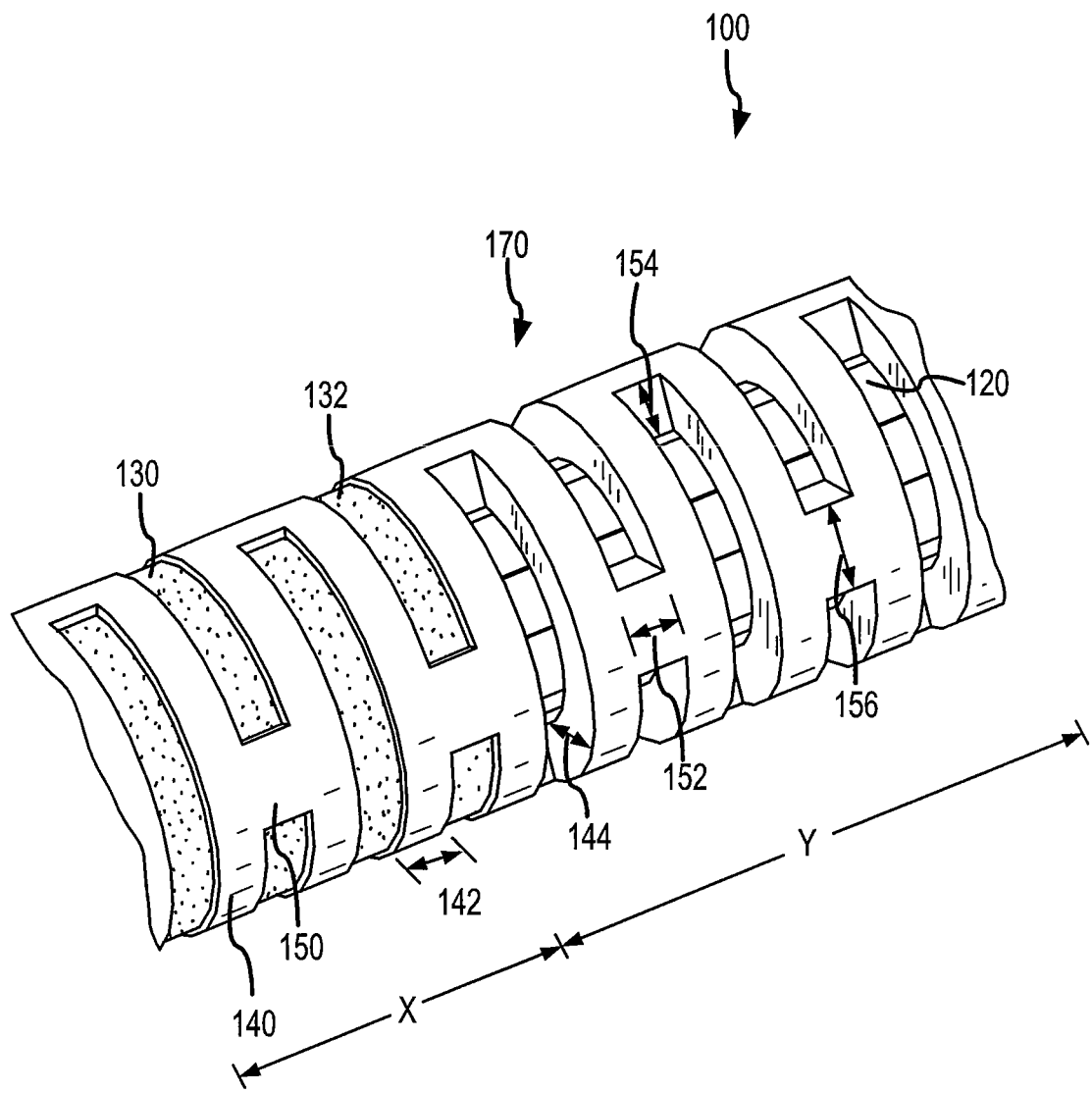
FIG. 12 shows a portion of an fiber optical guidewire according to embodiments of the present invention.

FIG. 12 illustrates aspects of an optical guidewire system 100 according to embodiments of the present invention. Optical guidewire system 100 includes a hypotube 110, a bundle of optical fibers 120, and an adhesive plug 130 that forms a joint bond where the optical fibers are fixed relative to the hypotube and to one another. Hypotube 110 includes an alternating series of circumferentially oriented hoops 140 and longitudinally oriented braces 150. Each hoop 140 has a hoop length 142 and a hoop depth 144. Each brace 150 has a brace length 152, a brace depth 154, and a brace width 156. As shown here, there are two braces between each two neighboring hoops, and the braces are disposed on opposing sides of the hypotube. Adhesive plug 130 may include projections 132 that extend radially outward from a central longitudinal axis of the hypotube. Projections 132 may be disposed between hypotube hoops 140 and braces 150. Often, a projection 132 extends radially outward so as to span the full distance of hoop depth 144 and brace depth 154.

For a typical hypotube, the presence of an adhesive plug 130 will impart greater stiffness to a guidewire than will the absence of an adhesive plug. Similarly, a longer hoop length 142 can impart greater flexibility than a shorter hoop length. A longer brace length 152 will typically impart a greater flexibility than a shorter brace length. A larger brace width 156 can impart greater stiffness than a smaller brace width. A larger hoop depth 144 or brace depth 154 can impart greater stiffness than a smaller hoop depth or smaller brace depth, respectively. Variations in hoop depth 144 and brace depth 154 can be introduce via tapering, boring, or grinding techniques that change the inner diameter and the outer diameter of the hypotube. Relatedly, techniques that vary the wall thickness of the hypotube can also vary the hoop depth and brace depth. In some embodiments, a hypotube is constructed by placing a cut 170 in the body of the hypotube, so as to form an aperture in the tube. Often, the cut will be made transverse to a central longitudinal axis of the hypotube. A deeper cut or slot 170 can result in a smaller brace width 156. Similarly, a more shallow cut 170 can result in a larger brace width 156. As shown here, a cut width can correspond to the brace length 152. In some embodiments, a brace length 152 can be within a range from about 0.001 inch to about 0.002 inch. In some cases, a brace length 152 can be within a range from about 0.002 inch to about 0.005 inch.

An exemplary method of forming such adhesive plugs includes placing a portion of the hypotube into a mold, pouring or injecting an adhesive into the mold, heating the adhesive so that it is wicked within the hypotube along the optical fibers, introducing cold air at one end of the mold so as to initiate setting of the adhesive. As noted above, adhesive can extend radially into spaces between the hoops and braces of the hypotube, and thus provide an anchor to prevent the optical fibers, and optionally the mandrel, from slipping longitudinally within the hypotube.

In some embodiments, an optical guidewire system may include a plurality of adhesive plugs. The adhesive plugs can be spaced at discrete locations along the length of the hypotube. For example, an optical guidewire system 100 may include one more sections X where there is an adhesive plug, and one or more sections Y where there is not an adhesive plug. At sections X, where there is an adhesive plug, the optical fibers are potted within the hypotube to create a composite structure. Thus, the individual fibers of the bundle are restricted from moving freely within the hypotube, and from moving relative to each other or relative to the hypotube. Such movement is also inhibited even when the guidewire system is bent or deflected. If the guidewire system includes a mandrel, the fibers may be bonded with the mandrel as well. At sections Y, where there is no adhesive plug, the individual fibers of the bundle can move freely within the hypotube, and can move relative to each other and relative to the hypotube. This allows the hypotube and each of the individual fibers to operate or function independently when the guidewire system is snaked through a tortuous vessel or lumen. Such freedom of movement can impart a component of flexibility to the guidewire system.

Figure 13:
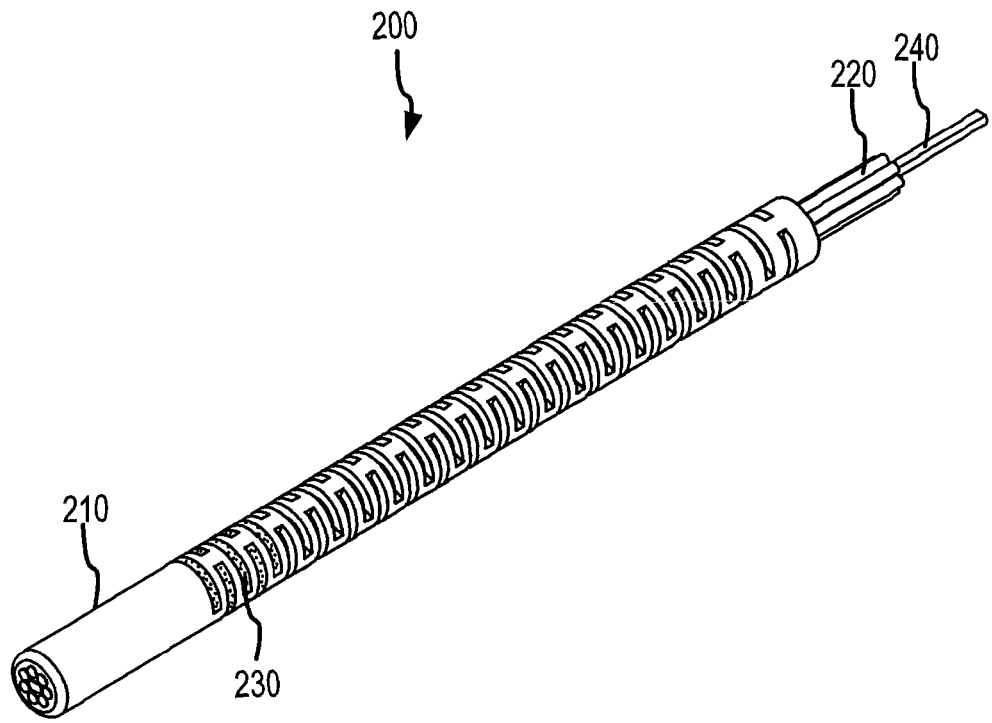
FIGS. 13 and 14 show fiber optical guidewires according to embodiments of the present invention.
Figure 14:
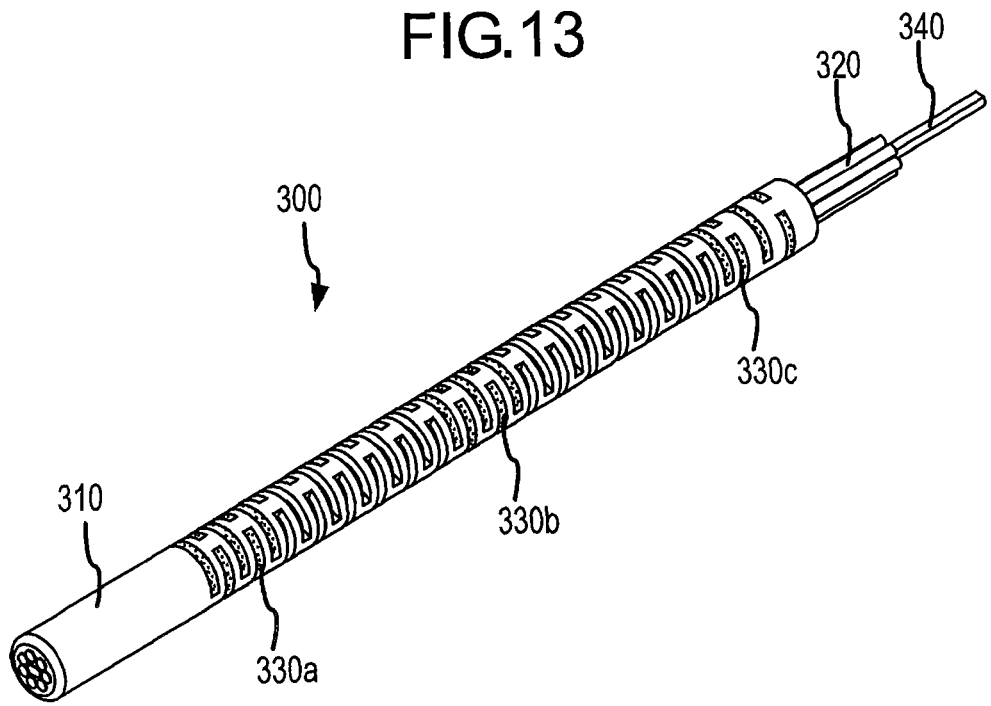

In an exemplary embodiment, as shown in FIG. 13, a guidewire system 200 can include a hypotube 210 with a bundle of optical fibers 220 and a mandrel 240 disposed therein. The optical fibers and mandrel are potted within the hypotube at the distal end of the hypotube with an adhesive plug 230. The cross section of the mandrel can provide two opposing flat sides and two opposing arcuate sides, similar to a flattened rod. In some embodiments, as shown in FIG. 14, a guidewire system 300 includes a hypotube 310 having a length of about 190 cm with a bundle of optical fibers 320 and a mandrel 340 disposed therein. The optical fibers are potted within the hypotube at the distal end of the hypotube with a first adhesive plug 330a, at an intermediate section located approximately 3 cm from the distal end of the hypotube with a second adhesive plug 330b, and at the proximal end of the hypotube, or at the proximal end of a proximal slotted section of the hypotube, approximately 30 cm from the distal end of the hypotube with a third adhesive plug 330c. The third adhesive plug can be disposed Each of these three bond joints can have a length within a range from about 3 cm to about 4 cm. The distal end of the core mandrel may be disposed at any desired location along the length of the hypotube. For example, the distal end of the mandrel may be disposed at or near the intermediate bond joint. In some cases, the system may not include a mandrel disposed on the interior of the fiber bundle.

Often, a mandrel will be constructed of a material that is more dense than the hypotube. A mandrel can operate as a security feature to the guidewire system so that if the hypotube breaks, the mandrel provides an additional structure within the system, thus serving to maintain or preserve the structural integrity of the system. Moreover, a mandrel can impart an additional degree or variability of stiffness to the guidewire system, depending on the material used to manufacture the mandrel and the configuration of the mandrel. The mandrel can also serve as a visualization feature, for example by incorporating radiopaque elements. In some embodiments, a mandrel can have a constant diameter or cross section along the length of the mandrel. In some embodiments, a mandrel can have a diameter or cross section that varies along the length of the mandrel. The diameter or cross-section can vary in a stepwise fashion or in a linear fashion along the length of the mandrel, for example. Such mandrel configurations can impart desirable flexibility profile configurations to a guidewire. In some cases, a variable stiffness mandrel can be combined with a variable stiffness hypotube. In some cases, a variable stiffness mandrel can be combined with a constant stiffness hypotube.

Figure 15:
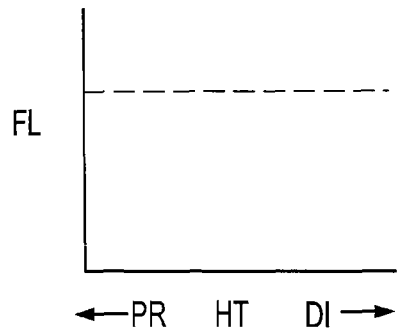
FIGS. 15, 16, 17, 18, and 19 show graphs depicting hypotube flexibility profiles according to embodiments of the present invention.
Figure 16:
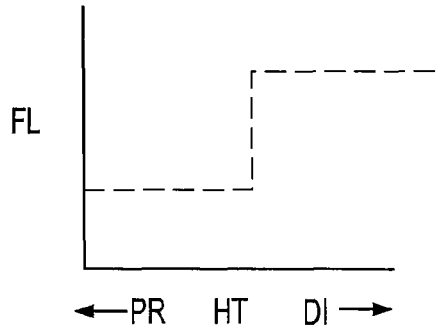

As illustrated in FIG. 12, adjacent hypotube hoops 140 can be separated by intervening braces 150. In some embodiments of the invention, each hoop has the same hoop length 142 and each brace has the same brace length 152. Such hypotube construction can provide a flexibility profile as shown in FIG. 15, where the flexibility FL of the hypotube is constant at each location HT along the length of the hypotube, from the proximal end PR to the distal end DI. Often, flexibility can be inversely related to bending stiffness. Optionally, the hypotube can be constructed so that it provides a first section where each hoop has a first hoop length 142 and each brace a first brace length 152 and a second section where each hoop has a second hoop length 142 and each brace a second brace length 152, such that the first and second hoop lengths are different and the first and second brace lengths are different. A hypotube having this configuration can provide a flexibility profile as shown in FIG. 16, where the flexibility FL of the hypotube increases as a discontinuous stepwise function at locations HT along the length of the hypotube, from the proximal end PR to the distal end DI. Spiral hypotubes having discrete stepped pitch regions, such as those shown in FIG. 9B, can also provide such a flexibility profile. Similarly, hypotubes having discrete stepped cut width regions can provide such flexibility profiles.

Figure 17:
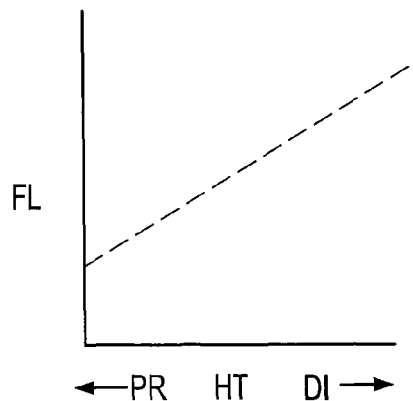
Figure 18:
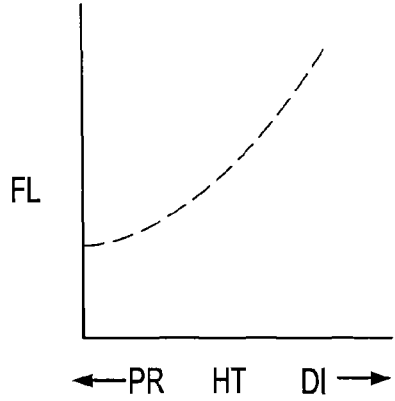
Figure 19:
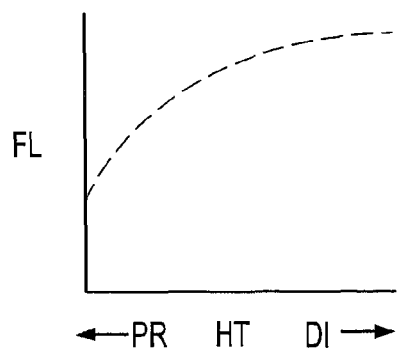

In another embodiment, each hoop has the same hoop length 142, and each brace has a brace length 152 that is longer than the brace length of the neighboring proximal brace. Hypotube configurations such as this can provide a flexibility profile as shown in FIG. 17, 18, or 19 depending on the degree to which brace length increases along the hypotube. For example, the increasing change in brace length may impart a flexibility profile where the flexibility FL increases in linear relationship to a particular location HT along the hypotube, from the proximal end PR to the distal end DI, as shown in FIG. 17. Relatedly, a linear flexibility profile such as that show in FIG. 17 can be achieved by a hypotube configuration where each hoop has a hoop length 142 that is shorter than the hoop length of the neighboring proximal hoop, and each brace has the same brace length 152. Similarly, hypotubes having a configuration where each brace has a brace length that is longer than the brace length of the neighboring proximal brace can provide such flexibility profiles.

Optionally, the increasing change in brace length may impart a flexibility profile where the flexibility FL increases in non-linear smooth and continuous relationship to a particular location HT along the hypotube, from the proximal end PR to the distal end DI, as shown in FIGS. 18 and 19. Relatedly, a non-linear continuous flexibility profile such as that show in FIGS. 18 and 19 can be achieve by a hypotube configuration where each hoop has a hoop length 142 that is shorter than the hoop length of the neighboring proximal hoop, and each brace has the same brace length 152, depending on the degree to which hoop length decreases along the hypotube.

Figure 20:
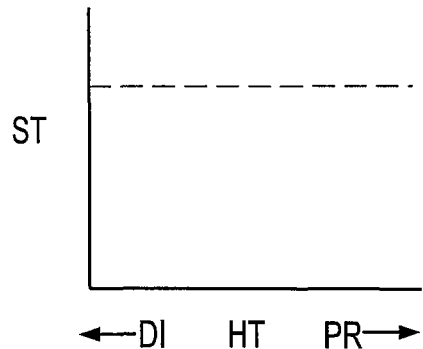
FIGS. 20, 21, 22, 23, and 24 show graphs depicting hypotube stiffness profiles according to embodiments of the present invention.
Figure 21:
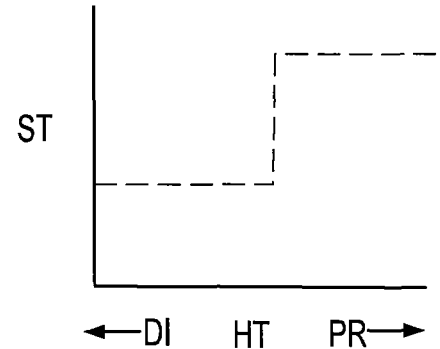

As noted above, adjacent hypotube hoops 140 can be separated by intervening braces 150. In some embodiments of the invention, each hoop has the same hoop length 142 and each brace has the same brace length 152. Such hypotube construction can provide a stiffness or bending stiffness profile as shown in FIG. 20, where the stiffness or bending stiffness ST of the hypotube is constant at each location HT along the length of the hypotube, from the proximal end PR to the distal end DI. Often, flexibility can be inversely related to bending stiffness. Optionally, the hypotube can be constructed so that it provides a first section where each hoop has a first hoop length 142 and each brace a first brace length 152 and a second section where each hoop has a second hoop length 142 and each brace a second brace length 152, such that the first and second hoop lengths are different and the first and second brace lengths are different. A hypotube having this configuration can provide a flexibility profile as shown in FIG. 21, where the stiffness ST of the hypotube increases as a discontinuous stepwise function at locations HT along the length of the hypotube, from the distal end DI to the proximal end PR. Spiral hypotubes having discrete stepped pitch regions, such as those shown in FIG. 9B, can also provide such a stiffness profile. Similarly, hypotubes having discrete stepped cut width regions can provide such stiffness profiles.

Figure 22:
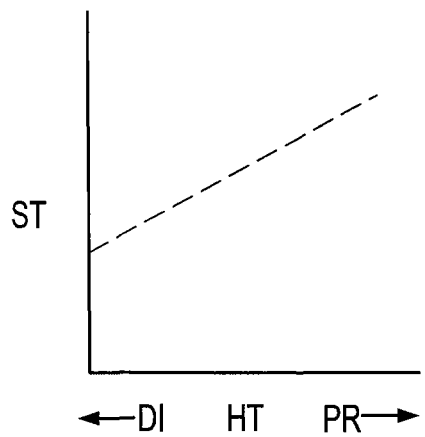
Figure 23:
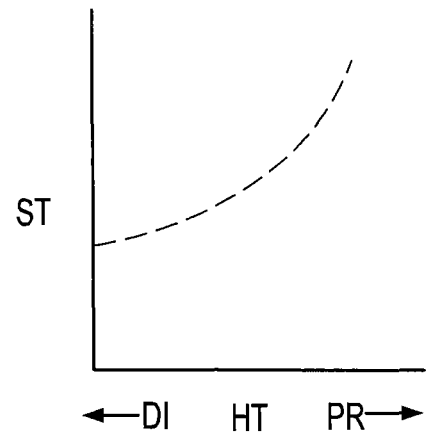
Figure 24:
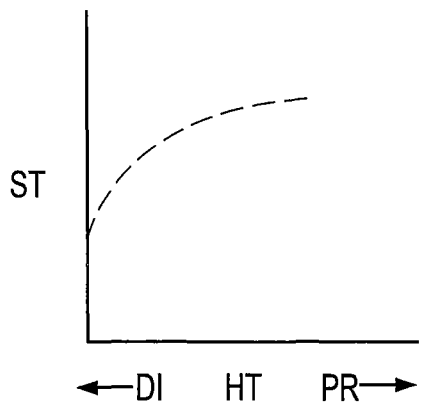

In another embodiment, each hoop has the same hoop length 142, and each brace has a brace length 152 that is longer than the brace length of the neighboring proximal brace. Hypotube configurations such as this can provide a stiffness profile as shown in FIG. 22, 23, or 24 depending on the degree to which brace length increases along the hypotube. For example, the increasing change in brace length may impart a stiffness profile where the stiffness ST decreases in linear relationship to a particular location HT along the hypotube, from the proximal end PR to the distal end DI, as shown in FIG. 22. Relatedly, a linear stiffness profile such as that show in FIG. 22 can be achieved by a hypotube configuration where each hoop has a hoop length 142 that is shorter than the hoop length of the neighboring proximal hoop, and each brace has the same brace length 152. Similarly, hypotubes having a configuration where each brace has a brace length that is longer than the brace length of the neighboring proximal brace can provide such stiffness profiles. In some cases, a linear stiffness profile such as that shown in FIG. 22 can be achieved by a hypotube having a constant stiffness profile in combination with a mandrel with a variable stiffness profile, or a hypotube having a constant stiffness profile in combination with one or more adhesive plugs that provide an overall variable stiffness profile.

Optionally, the increasing change in brace length may impart a stiffness profile where the stiffness ST decreases in non-linear smooth and continuous relationship to a particular location HT along the hypotube, from the proximal end PR to the distal end DI, as shown in FIGS. 23 and 24. Relatedly, a non-linear continuous stiffness profile such as that show in FIGS. 18 and 19 can be achieve by a hypotube configuration where each hoop has a hoop length 142 that is shorter than the hoop length of the neighboring proximal hoop, and each brace has the same brace length 152, depending on the degree to which hoop length decreases along the hypotube.

In some cases, the overall stiffness or flexibility profile of the guidewire is a composite profile that collectively reflects the individual stiffness or flexibility of the components parts of the guidewire, such as a hypotube, a mandrel, and an adhesive plug. The flexibility and stiffness profiles of the composite structure, or of any of the individual components or combinations thereof, can mirror or be similar to any of those profiles shown in FIGS. 15-24.

In some embodiments, bending stiffness can be defined as the slope of the force/deflection curve pursuant to a flexural test such as ASTM D790 (e.g. 3 point bend test with 1 inch span length). In one testing example, the distance between two idler wheels center to center, or between two contact or fulcrum points, is 1". The force measurement wheel or central contact or fulcrum point is centrally disposed equidistant from each of the two idler wheels. The deflection distance of the force measurement wheel, or at the center contact or fulcrum point, is 0.200". Embodiments of the present invention provide guidewires having a bending stiffness of about 0.04 grams at or near a proximal end where the hypotube is not slotted, 0.008 grams at or near a location about 15 cm from the distal end of the hypotube, and 0.004 grams at or near a location about 1 cm from the distal end of the hypotube. These force values correspond to a deflection distance of 0.200" in a one inch span 3 point bend test. Thus, stiffness can be characterized by the amount of force required to deflect a tip or section of a guidewire a given distance off of a known or linear path. Often, flexibility can be inversely related to stiffness. Still further, embodiments of the present invention encompass guidewires having a bending stiffness within a range from about 1 gram to about 0.01 grams at or near a proximal end where the hypotube is not slotted, where the stiffness force corresponds to a deflection distance of 0.200" in a one inch span 3 point bend test. Embodiments also encompass guidewires having a bending stiffness within a range from about 0.1 grams to about 0.001 grams at or near a location about 15 cm from the distal end of the hypotube, where the stiffness force corresponds to a deflection distance of 0.200" in a one inch span 3 point bend test. Embodiments also encompass guidewires having a bending stiffness within a range from about 0.05 grams to about 0.0001 grams at or near a location about 1 cm from the distal end of the hypotube, where the stiffness force corresponds to a deflection distance of 0.200" in a one inch span 3 point bend test.

In some embodiments, tip bending stiffness can be defined as the amount of longitudinal force applied to a distal section of the guidewire, or component thereof, required to deflect or bow that section of the guidewire from a linear alignment. An exemplary testing apparatus includes a flat surface or force plate coupled with a force gauge, and a clamp or holding device. The distal tip of the guidewire is contacted with the flat surface, so that the guidewire substantially perpendicular to the flat surface. The holding device is then coupled with the guidewire at a location proximal to the distal tip. The distance between the force plate and the holding device is the deflection distance. For example, the holding device can be coupled with the guidewire at about 1.2 cm from the distal tip in some tests. In some cases, the holding device can be coupled with the guidewire at about 2.0 cm from the distal tip. A longitudinal compression force is then applied to the section of the guidewire disposed between the flat surface and the holding device, and the force is increased until that section of the guidewire bends, bows, or otherwise deviates from a linear alignment. The amount of force measured at the time the guidewire bends thus reflects the tip bending stiffness. The results of series of exemplary tip bending stiffness tests involving embodiments of the present invention compared with a commercial mechanical guidewire are shown in Table 1. Embodiments 1-4 include optical fibers (number, diameter) and mandrel cores (diameter).

TABLE 1

| Device | Deflection Distance 1.2 cm | Deflection Distance 2.0 cm |
| --- | --- | --- |
| Commercial Device | 6 grams | 3 grams |
| Embodiment 1 8-45 micron fibers .002 flattened core | 3 grams | 1.2 grams |
| Embodiment 2 8-45 micron fibers .0025 flattened core | 3.5 grams | 1.6 grams |
| Embodiment 3 7-50 micron fibers .002 flattened core | 3.7 grams | 1.5 grams |
| Embodiment 4 7-50 micron fibers .0025 flattened core | 4.1 grams | 1.6 grams |

As shown in Table 1, Embodiment 1 includes 8 45 micron fibers and has a lower tip bending stiffness than Embodiment 3 which includes 7 50 micron fibers. Thus, a greater number of smaller fibers is more flexible than a smaller number of larger fibers, and the cumulative cross section of the smaller fibers (8*45=360) is larger than the cumulative cross section of the larger fibers (7*50=350). Even though Embodiment 1 has more fibers than Embodiment 3, it is less stiff than Embodiment 3. The data also shows that a larger core mandrel can impart a greater amount of stiffness. In some embodiments, a guidewire according to the present invention can have a distal tip bending stiffness within a range from about 3 grams to about 4 grams at a deflection distance of about 1.2 cm. In some embodiments, a guidewire can have a tip bending stiffness within a range from about 2 grams to about 5 grams at a deflection distance of about 1.2 cm. In related embodiments, a guidewire can have a tip bending stiffness within a range from about 1 gram to about 6 grams at a deflection distance of about 1.2 cm. In some embodiments, a guidewire can have a tip bending stiffness within a range from about 0.5 gram to about 8 grams at a deflection distance of about 1.2 cm. In some embodiments, a guidewire according to the present invention can have a distal tip bending stiffness within a range from about 1 gram to about 2 grams at a deflection distance of about 2 cm. In some embodiments, a guidewire can have a tip bending stiffness within a range from about 0.75 grams to about 2.25 grams at a deflection distance of about 2 cm. In related embodiments, a guidewire can have a tip bending stiffness within a range from about 0.5 grams to about 2.5 grams at a deflection distance of about 2 cm. In some embodiments, a guidewire can have a tip bending stiffness within a range from about 0.25 gram to about 5 grams at a deflection distance of about 2 cm.

In some embodiments, guidewires according to the present invention provide torque response characteristics similar to other commercially available mechanical guidewires which do not include hypotubes with variable stiffness characteristics, which include hypotubes with a greater mass than exemplary hypotube embodiments disclosed herein, or which include unslotted hypotubes. In a series of exemplary torque performance tests, it was observed that some embodiments of the present invention and other commercially available guidewires had a torque efficiency rating of about 80%. A torque efficiency rating can be defined as the amount of output rotation at the distal end of a guidewire divided by the amount of input rotation at the proximal end of the guidewire. For example, if the proximal end of the guidewire is rotated 360 degrees, and the distal end of the guidewire is observed to rotate 288 degrees, then the calculated torque efficiency rating is (288÷360=0.80) or 80%. In some cases, guidewire embodiments of the present invention were observed to have torque efficiency ratings within a range from about 70% to about 100%.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

What is claimed is:
1. A fiber optic guidewire comprising:
a hypotube having a monolithic body, the monolithic body including a proximal end and a distal end, the distal end having a distal end termination;
an adhesive plug within the distal end of the hypotube and having a distal face substantially flush with the distal end termination of the hypotube;
a plurality of optical fibers disposed within the hypotube, wherein the optical fibers extend through the adhesive plug and have a distal face terminating substantially at the distal face of the adhesive plug;
the adhesive plug surrounding the optical fibers and bonding the fibers within the distal end of the hypotube; and
the hypotube is comprised of at least one distal segment having an outer surface with a plurality of openings providing variable stiffness and tracking characteristics between at least one proximal segment and one distal segment of the guidewire, wherein the openings are formed by a plurality of hoops such that each hoop is coupled with an adjacent hoop via a brace, wherein the adhesive plug comprises projections that extend radially outward from a central longitudinal axis of the hypotube and within at least one of the plurality of openings, and wherein the hypotube is configured to transfer torque applied to the proximal segment through to the distal segment via the monolithic body of the hypotube.
2. The guidewire of claim 1, further comprising a mandrel disposed within the hypotube, with a distal end terminating substantially at the distal end of the hypotube, the mandrel cooperating with the optical fibers to permit the distal end of the hypotube to be shaped as desired by a user.

3. The guidewire of claim 1, wherein the hypotube comprises at least one proximal portion having a first stiffness and at least one distal portion having a second stiffness less than said first stiffness.

4. The guidewire of claim 1, further comprising a proximal coupler.

5. The guidewire of claim 1, wherein the hypotube comprises a member selected from the group consisting of stainless steel and Nitinol.

6. A fiber optic guidewire comprising:
   a hypotube having a monolithic body, the monolithic body including a proximal end, a distal end, and a segment having an outer surface with a plurality of openings providing variable stiffness and tracking characteristics to the hypotube, wherein the openings are formed by a plurality of hoops such that each hoop is coupled with an adjacent hoop via a brace, and wherein the hypotube is configured to transfer torque applied to the proximal end through to the distal end via the monolithic body of the hypotube;
   two or more optical fibers disposed within the hypotube; and
   an adhesive plug within the hypotube that surrounds the optical fibers and bonds them to the hypotube, wherein the adhesive plug comprises projections that extend radially outward from a central longitudinal axis of the hypotube and within at least one of the plurality of openings.

7. The guidewire of claim 6, further comprising a mandrel disposed within the hypotube.

8. The guidewire of claim 6, wherein the hypotube comprises at least one proximal portion having a first stiffness and at least one distal portion having a second stiffness less than said first stiffness.

9. The guidewire of claim 6, wherein the hypotube has a flexibility that increases as a linear function of a position along the hypotube extending from a proximal location to a distal location.

10. The guidewire of claim 6, wherein the hypotube has a flexibility that increases as a smooth and continuous function of a position along the hypotube extending from a proximal location to a distal location.

11. The guidewire of claim 6, wherein a length of each hoop is constant.

12. The guidewire of claim 6, wherein a length of each brace is constant.

13. The guidewire of claim 6, wherein a length of each hoop is smaller than the length of a proximal adjacent hoop.

14. The guidewire of claim 6, wherein the adhesive plug is disposed toward the distal end of the hypotube, the guidewire further comprising a second adhesive plug within the hypotube disposed between the distal and proximal ends of the hypotube that surrounds the optical fibers and bonds them to the hypotube, and a third adhesive plug within the hypotube disposed toward the proximal end of the hypotube that surrounds the optical fibers and bonds them to the hypotube.

15. The guidewire of claim 6, further comprising a radiopaque material on or in the hypotube.

16. The guidewire of claim 6, further comprising a hydrophilic material on the hypotube.

17. The guidewire of claim 6, wherein the guidewire comprises a torque efficiency rating within a range from about 70% to about 100%.

18. The guidewire of claim 6, wherein the guidewire comprises a distal tip bending stiffness within a range from about 1 gram to about 6 grams at a deflection distance of about 1.2 cm and a distal tip bending stiffness within a range from about 0.25 gram to about 5 grams at a deflection distance of about 2 cm.

19. The guidewire of claim 6, wherein the guidewire comprises a bending stiffness within a range from about 0.05 grams to about 0.0001 grams at or near a location about 1 cm from the distal end of the hypotube, where the bending stiffness corresponds to a deflection distance of 0.200" in a one inch span 3 point bend test.

20. A method of manufacturing a guidewire, comprising:
   providing a hypotube having a monolithic body, the monolithic body including a proximal end and a distal end, and a plurality of apertures disposed in a wall of the hypotube between the proximal end and the distal end, wherein the apertures are formed by a plurality of hoops such that each hoop is coupled with an adjacent hoop via a brace, wherein the distal end comprises a distal end termination;
   placing two or more optical fibers at least partially within the hypotube, wherein the two or more optical fibers terminate substantially at the distal end of the hypotube;
   introducing an adhesive material into the hypotube, and allowing the material to wick along the optical fibers and into at least one of the plurality of apertures of the wall of the hypotube, such that the adhesive material forms an adhesive plug that fixes the optical fibers relative to the hypotube; and
   polishing the distal end of the hypotube, such that the adhesive plug, the two or more optical fibers, and the distal end of the hypotube form a distal face substantially flush with the distal end termination of the hypotube.

21. The method of claim 20, further comprising inserting a mandrel at least partially within the hypotube.

22. The method of claim 20, wherein the guidewire comprises at least one proximal portion having a first stiffness and at least one distal portion having a second stiffness less than the first stiffness.

* * * * *